United States Patent [19]

Bru

[11] Patent Number: 4,614,648

[45] Date of Patent: Sep. 30, 1986

[54] PROCESS FOR MANUFACTURING EFFERVESCENT GRANULES AND TABLETS

[76] Inventor: Jean Bru, 24 Rue Raphael, Paris 75016, France

[21] Appl. No.: 643,980

[22] PCT Filed: Dec. 20, 1983

[86] PCT No.: PCT/FR83/00253

§ 371 Date: Aug. 20, 1984

§ 102(e) Date: Aug. 20, 1984

[87] PCT Pub. No.: WO84/02468

PCT Pub. Date: Jul. 5, 1984

[30] Foreign Application Priority Data

Dec. 21, 1982 [FR] France .............................. 82 21476
Nov. 30, 1983 [FR] France .............................. 83 19143

[51] Int. Cl.$^4$ .......................... A61L 9/04; B01F 3/12; C06D 5/10
[52] U.S. Cl. ................................ 424/44; 252/188.31; 252/350; 252/363.5; 514/163; 514/474; 514/629; 514/960; 514/961
[58] Field of Search .................. 252/157, 188.31, 350, 252/363.5; 424/44; 514/960, 961

[56] References Cited

U.S. PATENT DOCUMENTS

| | | | |
|---|---|---|---|
| 2,463,962 | 3/1949 | Gorcica et al. | 252/188.31 X |
| 2,497,057 | 2/1950 | Pape et al. | 252/188.31 X |
| 2,985,562 | 5/1961 | Millard et al. | 424/44 |
| 2,999,293 | 9/1961 | Taff et al. | 424/44 X |
| 3,401,216 | 9/1968 | Coletta | 424/44 X |
| 3,480,185 | 11/1969 | Steinberg et al. | 252/350 X |
| 3,773,922 | 11/1973 | Gergely | 252/188.31 X |
| 3,903,255 | 9/1975 | Gusman et al. | 424/44 |
| 4,267,164 | 5/1981 | Yeh et al. | 424/44 |

FOREIGN PATENT DOCUMENTS

| | | | |
|---|---|---|---|
| 0011489 | 5/1980 | European Pat. Off. | 424/44 |
| 0076340 | 4/1983 | European Pat. Off. | |
| 2092893 | 1/1972 | France . | |

*Primary Examiner*—Richard D. Lovering
*Attorney, Agent, or Firm*—Ostrolenk, Faber, Gerb & Soffen

[57] ABSTRACT

The invention relates to a process for manufacturing effervescent tablets consisting in the steps of careful humidifying of the acid+base mixture, pre-drying and final drying and granulating.

It has been found that these operations can be performed in a single apparatus, either integrally in fluid bed, or with vacuum-drying.

9 Claims, 2 Drawing Figures

PROCESS FOR MANUFACTURING EFFERVESCENT GRANULES AND TABLETS

The present invention relates to an improved process for manufacturing effervescent mixtures and tablets containing in particular active principles for pharmaceutical use.

In this domain, positive progress has been made by the techniques described in French Pat. Nos. 71 12175 and 71 35069.

These techniques employ three stages of operation:
(1) Careful humidification of the sodium bicarbonate by a very small quantity of demineralized water, then addition of citric acid and possibly of glycocoll (binding agent), all this in a mixer of the kneader type, which starts off the reaction of the bicarbonate on the citric acid;
(2) pre-drying of the mixture in fluid bed obtained by blowing hot air, which interrupts the reaction;
(3) final drying, likewise in fluid bed, obtained by blowing hot air.

The two Patents mentioned above describe with precision the details of the modus operandi for each of the three phases: duration, temperature of the air, humidity content, speed of the air jet, etc., and the man skilled in the art may usefully refer to them.

Although very interesting, this technique presents the drawback of necessitating the transfer of the filler, after step (1), from the mixer to the drier. Consequently, the effervescent reaction triggered off in the mixer cannot be mastered with total precision as its interruption, which occurs in step (2) in the drier, depends on the time for emptying and transferring the filler towards the drier, which time varies from one batch to the following.

This variation in time has a considerable repercussion on the quality of the grain at the end of granulation.

No solution to this problem of industrial working has been found since the invention of the technique, about twelve years ago, despite the obvious interest in solving it and the attempts which have been made to that end.

It has now been discovered, according to the invention, that all of the reactions and operations described hereinabove can be carried out in one and the same multi-function apparatus.

Taking into account the very high precision required in these operations in order to satisfy the very strict quality requirements laid down by the pharmaceutical industry (particularly concerning the homogeneity of the finished granule, and the interruption at a very precise degree of advance of the reaction initiated by the addition of solvent), this was not considered possible.

However, Applicant has achieved this result and, moreover, has also improved the quality of the granules.

BRIEF DESCRIPTION OF THE DRAWINGS

The invention will be more readily understood on reading the following description with reference to the accompanying drawings, in which.

Figure 1:
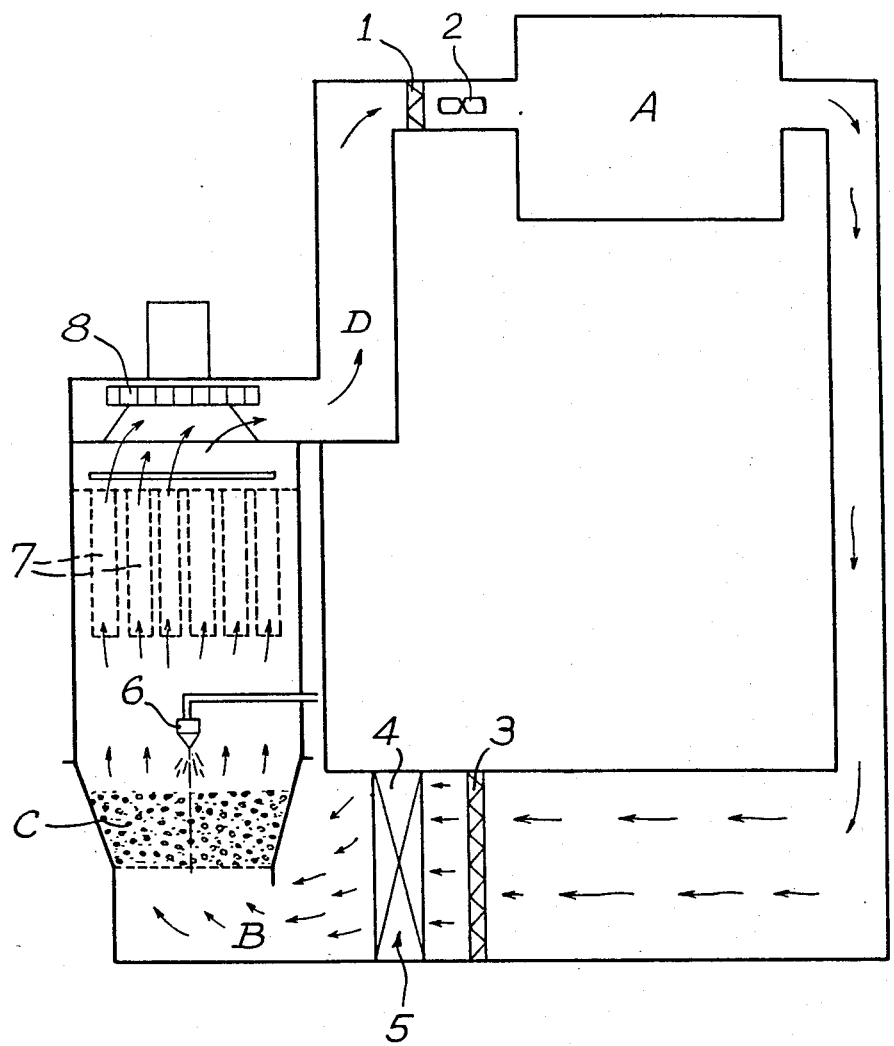
FIG. 1 shows the apparatus, and in particular the granulator-drier, used for the tests referred to hereinbelow according to one variant embodiment of the invention.

The references in FIG. 1 have the following meanings:
A: hygrometric treatment of the air
B: dry incoming air
C: powder in suspension
D: humid outgoing air
1, 3 and 7: filters
2 and 8: turbines
4: heating element
5: heat regulating system
6: solvent spray The operation of such an apparatus is obvious and is, moreover, generally known.

Figure 2:
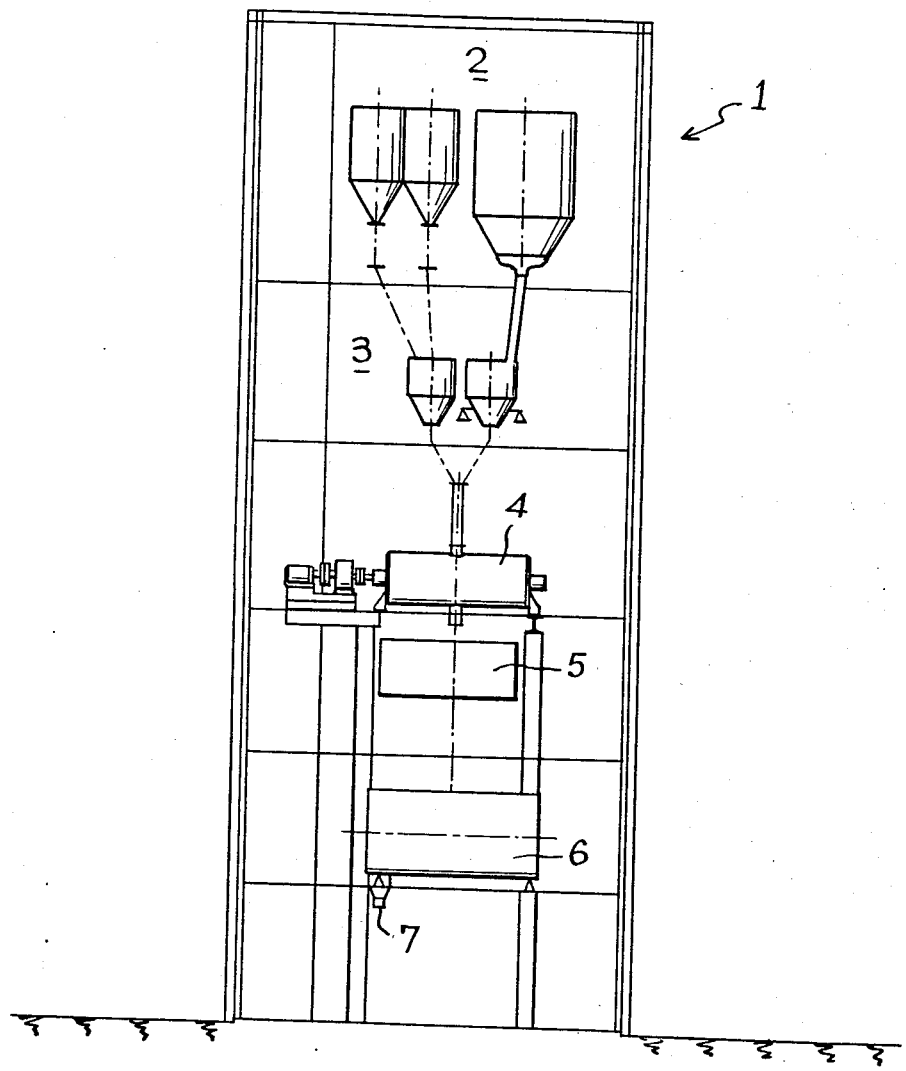

FIG. 2 schematically shows the arrangement of apparatus according to another variant of the invention in a production tower.

In FIG. 2, the references have the following meanings:
1. production tower
2. storage hoppers
3. automatic supply
4. mixing-granulation-drying apparatus
5. heat exchange hopper
6. band mixer
7. emptying

DESCRIPTION

According to a first variant of the invention (FIG. 1), a granulator-drier operating entirely in fluid bed is used.

Granulator-driers of the type which will be described hereinafter have been known for a long time.

However, it was not thought possible that the turbulence created in such apparatus by the blowing of air could suffice to suitably "imbricate" the particles of the starting reactive materials, which is essential in the technical sector in question, and it was thought, on the contrary, that only a "mechanical" stirring, i.e. of the type obtained by the blades in the mixers used in the prior known technique, could give a valid result. This is why no attempt has ever been made to use the granulator-driers, which are nonetheless well known.

It has now been unexpectedly discovered that these apparatus enable the particles of the starting material used in the technique in question to be correctly imbricated.

It is therefore possible to carry out the three operational steps mentioned above in one and the same apparatus, with the following very important advantages both as regards the quality of the products and industrial profitability:

no emptying or transfer of the reaction mixture, therefore providing the possibility of interrupting the effervescent reaction in extremely precise manner; this in turn leads to the disappearance of the differences which might be noted from one batch to another in the prior known technique;

saving of time the conventional mixers had to be placed under aspiration in order to avoid a rise in pressure due to the formation of $CO_2$. In addition, they had to be regularly unclogged. These two factors caused considerable losses of powder, which are not found in the new process according to the invention (about 1%);

possibility of calculating parameters of and automating the granulator-driers used, which was very difficult, if not impossible, in the prior known technique.

The principle of wet granulation used makes it possible to obtain, from powders of defined calibre, an elaborate product whose granulometric characteristics are adapted for subsequent compression.

This process of granulation also enables mixtures of powders of homogeneous chemical composition to be obtained by using fluidization.

Granulation consists in a fixation by chemical bond of the particles of sodium bicarbonate and of citric acid. These chemical bonds are obtained by an addition of a defined quantity of demineralized water which provokes a partial effervescent reaction with the formation of mono-, di- or trisodium citrate. These molecules of sodium citrate are considered as bridges bonding the particles of sodium bicarbonate and the particles of citric acid and give the mixture the physical properties of compressibility.

The effervescent reaction triggered off by an outside addition of 1 to 6% by weight of aqueous solvent (water or wetting solution) will continue by itself as it is generative of water, and it will be interrupted by drying by means of hot dry air (60°–70° C.).

The proces of granulation-drying is applicable in particular to the production of an excipient type effervescent mixture on which the active principles and lubricants are added in a subsequent operation; by way of example, we shall cite the parameters defined for buffered effervescent aspirin, for which a wet-process granulation is effected on 3 compounds: sodium bicarbonate, citric acid and possibly glycocoll (binding agent).

It is also applicable to the production of an effervescent mixture containing one or more active principles. By way of example, we shall cite the parameters defined for a formula containing paracetamol.

According to a second variant, the invention enables a process of production employing a vacuum to be carried out in particularly effective manner. This technique makes it possible:

to eliminate the separate wetting and drying phase
to shorten production time, thus improving productivity
to save energy
without forgetting the lesser risk of chemical destabilization by a treatment from solvents.

A further original feature of the invention resides in the fact that the apparatus have been grouped together in a vertical production tower.

According to this second variant (FIG. 2), the process for producing effervescent granules intended for compression is characterized by the creation of a tower 1 in which the following operations are carried out:

1. The weighing of raw materials from storage hoppers 2,
2. the automatic supply (3) of all or part of these raw materials in the mixer-granulator-drier 4,
3. the mixing, granulation and drying of the effervescent granule in vacuo,
4. the cooling in a heat exchange hopper 5 by fluidization more compact than a drier employing fluidized air bed,
5. calibration by oscillating granulator and final mixing in a band mixer 6 for example of the Gondard type on scales for calculating the yield,
6. emptying (7) of this mixer into containers of the Flo-Bin type.

Operations 1 to 6 occur vertically downwardly, transfers taking place by gravity and being dustfree. The interest resides in the fact that the 3 operations of point 3 (mixing, granulation, drying) can be automated from the standpoint of monitoring of the process.

Similarly, operations 1 to 5 in their chronological sequence may be automated. Such automatization renders the process economical from the standpoint of manpower (about 1 t/hr. for 2 persons) by elimination of the interruptions between the operations.

The apparatus serving for mixing-granulation-drying is composed of a perfectly sealed tank, provided with a system of mechanical stirring for mixing the incorporated powders and equipped with lump-breaking cutters which divide the agglomerates formed by the solvent during wetting. This tank must also comprise:

a double wall allowing passage of a heat-exchanging fluid
a trap for admission and emptying of the raw materials
a vacuum-creating apparatus which enables a minimum pressure of 70 millibars to be obtained.

All the mechanical or physical elements intervening in the successive operations of granulation-drying are monitored by thermometric probe, by measurement of amperage and vacuum.

By way of example, an apparatus of the adapted DVT Lödige type is suitable. A further originality of the invention resides in the use of a heat exchange hopper for cooling the granules.

The following Examples illustrate the invention without, however, limiting the scope thereof. For the general modus operandi, reference will be made to the above-mentioned French Patents. Examples 1 to 4 relate to the first variant, and I and II to the second variant of the invention.

EXAMPLE 1 reactive principle: aspirin
effervescent mixture:
    sodium bicarbonate
    citric acid
    glycocoll (optional)
for 255.22 kg of powder.

Operation 1: Premix

Incorporate successively the sodium bicarbonate, the citric acid and the glycocoll; switch on the turbine of the granulator at an output allowing fluidization of the powders.

Air temperature: 64° C.

Operation 2: Spraying

Solvent = demineralized water
The solvent is always sprayed on the powders in suspension in air, which makes it possible to increase the exchange surface between the base particles and the acid particles; at this stage of operation, the output and spray time must be monitored.

Operation 3: Drying

The rate of flow of air is to be monitored so as to avoid too great a turbulence of the powders in the cavity of the apparatus, which would render the particles fragile.

Temperature of incoming air: 64° C.

EXAMPLE 2

Granulation on granulator-drier of an effervescent mixture containing a plurality of active principles.

| Formula of granulation | |
|---|---|
| Paracetamol | 28 kg |

-continued

| Formula of granulation | |
| --- | --- |
| Monosodium carbonate | 100 kg |
| Monopotassium carbonate | 3.740 kg |
| Sorbitol | 25.500 kg |
| Anhydrous citric acid | 73.000 kg |
| Ascorbic acid | 17.000 kg |
| TOTAL | 247.24 kg |

Operation 1: Premix

Operation is carried out as in Example 1.
Air temperature: 64° C.

Operation 2: Spraying

Nature of the solvent: solvent of manoxol in water
Operation is carried out as in Example 1.

Operation 3: Drying

Temperature of air: 64° C.
Operation is carried out as in Example 1.
For the following two Examples, operation is carried out as in Examples 1 and 2, from the formulations hereinbelow:

EXAMPLE 3

| Disodium sulfate | 20.200 kg |
| --- | --- |
| Sodium bromide | 7.100 kg |
| Disodium phosphate | 13.800 kg |
| Monosodium carbonate | 101.000 kg |
| Anhydrous citric acid | 89.000 kg |

Nature of the solvent: aqueous solution by doxylamine succinate

EXAMPLE 4

| Monosodium carbonate | 108.000 kg |
| --- | --- |
| Anhydrous citric acid | 14.500 kg |
| Betaine citrate | 142.000 kg |

Nature of the solvent: demineralized water.

Example I—Example of granulation

Formulation
 paracetamol
 vitamin C
 sodium bicarbonate
 citric acid
 potassium bicarbonate
 sorbitol.

The tests were carried out on a mixture of the 58 kg of powders.

Operation 1: Premix

The different raw materials mentioned above are successively incorporated in the mixer 4 without taking into account any physical incompatibilities existing therebetween. The premix is effected in 3 minutes. During this period of time, the temperature of the powder is raised by introducing a heat-exchange liquid in the double jacket of the mixer.

Operation 2: Incorporation of the solvent in the mixer

The solvent is a mixture of water/sodium dioctylsulfosuccinate.

Wetting by spraying, or aspiration of the solvent under partical vacuum.
Concentration of the solvent: 0.64% with respect to the weight of the powder.

Operation 3: Granulation

Granulation is effected under atmospheric pressure for 5 minutes.

Operation 4: Drying

This is obtained by reducing the atmospheric pressure to 70 millibars; at that pressure, the boiling point of the solvent is attained. Drying continues by raising the temperature.

This operation lasts about 37 minutes, stoppage of drying being triggered off by monitoring the residual humidity of the powder.

The advantages of this technique are as follows:
obtaining of a granule of better quality, in particular one which is more homogeneous,
use of sufficiently low thermal zones, for the thermolabile active products not to be destabilized,
complete automation possible,
the addition of heat necessary for evaporation of the solvent is very little.

Example II—Example of mixing by direct compression

Formulation:
 Calcium carbasalate
 Lysine carbamate
 Citric acid
 Aroma
 PEG (polyethylene glycol)
 Ammonium saccharinate Description of manufacture (1) The calcium carbasalate will be stored in one of hoppers 2. It will then be pre-weighed at 3 and incorporated in the mixer-granulator-drier 4.

In this variant of the invention, the automation of the tower makes it possible to eliminate the functions of mixing and granulation and to conserve only the drying function of apparatus 4.

(2) After drying, the calcium carbasalate is sent into cooler 5 in order to return the product to its initial temperature.

(3) Calibration is effected, either by simple passage over a grid, or by crushing, the choice being made as a function of the nature of the products delivered.

(4) Emptying into a band mixer 6 in which the product is exactly weighed.

The four operations mentioned above are then repeated for the lysine carbamate and the citric acid.

After reception of these three constituents in the mixer, the auxiliary constituents: aroma, PEG and ammonium saccharinate, are added into the band mixer.

The running of the mixer and its working principle guarantee the required quality of the active principle of this formula from the standpoint of homogeneity.

What is claimed is:

1. A process for the manufacture of effervescent tablets in which the powdered raw materials therefor are mixed and the mixture is carefully humidified by a solvent followed by granulation and drying, wherein the steps of mixing said raw materials, humidifying the mixture with the solvent and drying are conducted inside the same apparatus, wherein the drying step is performed in vacuo.

2. The process of claim 1, wherein the components of the mixture are:
effervescent mixture:
sodium bicarbonate
citric acid
and the solvent is demineralized water.

3. The process of claim 2, wherein the effervescent mixture contains glycocoll.

4. The process of claim 1, wherein the mixture comprises:
paracetamol
monosodium carbonate
monopotassium carbonate
sorbitol
anhydrous citric acid
ascorbic acid
and the solvent is a solution of manoxol in water.

5. The process of claim 1, wherein said apparatus comprises in particular:
mixing means
means for introducing the solvent
means for regulating the temperature
means for creating a vacuum,
and drying is obtained in this apparatus by creating a vacuum.

6. The process of claim 5, wherein the granules are then cooled by passing in a heat exchange hopper.

7. The process of claim 5, wherein the mixing means comprises a system of mechanical stirring with lump-breaking cutters, the means for introducing the solvent comprises a system of aspiration of the solvent by creation of a vacuum or a spraying system supplied by a pump, and the means for regulating the temperature comprises a double jacket where a heat-exchange fluid circulates.

8. The process of claim 7, wherein the raw materials in powder form are as follows:
paracetamol
vitamin C
sodium bicarbonate
citric acid
potassium bicarbonate
sorbitol.

9. A process as claimed in claim 5 wherein the raw materials in powdered form are as follows:
calcium carbasalate
lysine carbamate
citric acid.

* * * * *